(12) United States Patent
Ho et al.

(10) Patent No.: US 9,902,997 B2
(45) Date of Patent: Feb. 27, 2018

(54) KIT COMPRISING A POLYNUCLEOTIDE PROBE FOR DETECTING A TARGET NUCLEIC ACID

(71) Applicant: National Taiwan University, Taipei (TW)

(72) Inventors: Ja-An A. Ho, Taipei (TW); Amily F. Jou, Taipei (TW); Yen-Chuan Ou, Taipei (TW); Shian-Shiang Wang, Taipei (TW); Itamar Willner, Taipei (TW); Shih-Lan Hsu, Taipei (TW)

(73) Assignee: National Taiwan University, Taipei (TW)

( * ) Notice: Subject to any disclaimer, the term of this patent is extended or adjusted under 35 U.S.C. 154(b) by 121 days.

(21) Appl. No.: 14/538,695

(22) Filed: Nov. 11, 2014

(65) Prior Publication Data

US 2016/0130653 A1 May 12, 2016

(51) Int. Cl.
*C12Q 1/68* (2006.01)
*C07H 21/02* (2006.01)
*C07H 21/04* (2006.01)

(52) U.S. Cl.
CPC ......... *C12Q 1/6886* (2013.01); *C12Q 1/6816* (2013.01); *C12Q 2600/178* (2013.01)

(58) Field of Classification Search
None
See application file for complete search history.

(56) References Cited

PUBLICATIONS

GenBank Accession No. AZ867664, Feb. 21, 2001, NCBI Database (National Center for Biotechnology Information, National Library of Medicine (Bethesda, MD, USA).*
Zuo et al ChemBioChem. 2011. 12: 2745-2747.*
Jou et al Chem Sci. published online Sep. 9, 2014. 6: 659-665.*
Ahern, H. The Scientist. Jul. 1995. 9(15): 20-25.*
Freeman et al Nano Letters. Sep. 12, 2011. 11:4456-4461.*
Freeman et al Analytical Chemistry. Jun. 18, 2012. 84: 6192-6198.*
Freeman et al American Chemcial Society Appl. Mater. Interfaces. Feb. 20, 2013. 5: 2815-2834.*
New England BioLabs. Products > NEBuffer 1. Available via url: <.neb.com/products/b7001-nebuffer-1>, printed on Jul. 11, 2017.*
Jemal, A., Siegel, R., Xu, J. & Ward, E. Cancer Statistics. Cancer J. Clin. 60, 277-300 (2010).
Schröder, F. H. & Roobol, M. J. Defining the optimal prostate-specific antigen threshold for the diagnosis of prostate cancer. Curr. Opin. UroL 19, 227-231 (2009).

(Continued)

*Primary Examiner* — Carla J Myers
(74) *Attorney, Agent, or Firm* — Mintz Levin Cohn Ferris Glovsky and Popeo, P.C.; Peter F. Corless; Joohee Lee

(57) ABSTRACT

The present invention provides a method for detecting a target nucleic acid that comprises a step of providing a sample; contacting the sample with a polynucleotide probe comprising a first sequence and a second sequence complementary to the target nucleic acid; and adding a nuclease for cleaving the second sequence of the polynucleotide probe. The present invention further provides a polynucleotide probe for detecting a target nucleic acid that comprises a first sequence and a second sequence complementary to the target nucleic acid. Moreover, the present invention provides a kit for detecting a target nucleic acid.

8 Claims, 6 Drawing Sheets

(56) References Cited

PUBLICATIONS

Kirsten L., G. et al. Valodation of the Kattan Preoperative Nomogram for Prostate Cancer Recurrence Using a Community Based Cohort: Results from Cancer of the Prostate Strategic Urological Research Endeavor (capsure). J. Urol.171, 2255-2259 (2004).

Catto, J. W. F. et al. Distinct MicroRNA Alterations Characterize High and Low-Grade Bladder Cancer. Cancer Res.69, 8472-8481 (2009).

Blenkiron, C. et al. MicroRNA expression profiling of human breast cancer identifies new markers of tumor subtype. Genome BioL 8, R214 (2007).

Mitchell, P. S. et al. Circulating microRNAs as stable blood-based markers for cancer detection. Proc. Nat. Acad. Sci. U.S.A. 105, 10513-10518 (2008).

Liu, S. et al Enzyme-free and ultrasensitive electrochemical detection of nucleic acids by target catalyzed hairpin assembly followed with hybridization chain reaction. Biosens. Bioelectron.49, 472-477 (2013).

Shimron, S., Wang, F., Orbah, R. & Willner, I. Amplified Detection of DNA through the Enzyme-Free Autonomous Assembly of Hemin/G-Quadruplex DNAzyme Nanowires. Anal. Chem.84, 1042-1048 (2012).

Wang, F., Elbaz, J., Orbah, R., Megan, N. & Whiner, I. Amplified Analysis of DNA by the Autonomous Assembly of Polymers Consisting of DNAzyme Wires. J. Am. Chem. Soc. 133, 17149-17151 (2011).

Weizmann, Y. et al. A Virus Spotlighted by an Autonomous DNA Machine. Angew. Chem., Int. Ed. 45, 7384-7388 (2006).

Orbach, R., Mostinski, L., Wang, F.&Willner, I. Nucleic Acid Driven DNA Machineries Synthesizing Mg2+-Dependent DNAzymes: An Interplay between DNA Sensing and Logic-Gate Operations. Chem. Eur. 118, 14689-14694 (2012).

Wang, F., Freage, L., Orbah, R.&Willner, I.Autonomous Replication of Nucleic Acids by Polymerization/Nicking Enzyme/DNAzyme Cascades for the Amplified Detection of DNA and the Aptamer-Cocaine Complex. Anal. Chem. 85, 8196-8203 (2013).

Tian, Y., He, Y.&Mao, C. Cascade Signal Amplification for DNA Detection. ChernBioChem.7, 1862-1864 (2006).

Wen, Y. et al., DNAzyme-Based Rolling-Circle Amplification DNA Machine for Ultrasensitive Analysis of MicroRNA in *Drosophila* Larva. Anal. Chem.84, 7664-7669 (2012).

Li, B., Jiang, Y., Chen, X .& Ellington, A. D. Probing Spatial Organization of DNA Strands using Enzyme-free Hairpin Assembly Circuits. J. Am. Chem. Soc.134, 13918-13921 (2012).

Dirks, R. M. & Pierce, N. A Triggered amplification by hybridization chain reaction. Proc. Natl. Acad. Sci. U.S. A.101,15275-15278 (2004).

Lin, Z. et al. An ultrasensitive colorimeter assay strategy for p53 mutation assisted by nicking endonuclease signal amplification. Chem. Commun. 47, 9069-9071 (2011).

Tian, T. et al. Sensitive and Convenient Detection of microRNAs Based on Cascade Amplification by Catalytic DNAzymes. Chem. Eur. J. 19, 92-95 (2013).

Bi, S., Zhang, S. & Zhang, S.Ultrasensitive and selective DNA detection based on nicking endonuclease assisted signal amplification and its application in cancer cell detectionw. Chem. Commun. 46, 5509-5511 (2010).

Zuo, X., Xia, F., Xiao, Y. & Plaxco, K. W. Sensitive and Selective Amplified Fluorescence DNA Detection Based on Exonuclease III-Aided Target Recycling. J. Am. Chem. Soc.132, 1816-1818 (2010).

Gill, R., Zayats, M. & Willner, I.Semiconductor Quantum Dots for Bioanalysis. Ange-w. Chem. Int. Ed.47, 7602-7625 (2008).

Frasco, M. F. & Chaniotakis, N.Semiconductor Quantum Dots in Chemical Sensors and Biosensors. Sensors 9,7266-7286 (2009).

Peng, H. et al.DNA Hybridization Detection with Blue Luminescent Quantum Dots and Dye-Labeled Single-Stranded DNA. J. Am. Chem. Soc. 129, 3048-3049 (2007).

Niazov, A., Freeman, R., Girsh, J.&Willner, I.Following Glucose Oxidase Activity by Chemiluminescence and Chemiluminescence Resonance Energy Transfer (CRET) Processes Involving Enzyme-DNAzyme Conjugates. Sensors 11, 10388-10397 (2011).

Freeman, R., Liu, X.&Willner, I. Chemiluminescent and Chemiluminescence Resonance Energy Transfer (CRET) Detection of DNA, Metal Ions, and Aptamer_Substrate Complexes Using Hemin/G-Quadruplexes and CdSe/ZnS Quantum Dots. J. Am. Chem. Soc.133, 11597-11604 (2011).

Sharon, E., Freeman, R.& Willner, I. CdSe/ZnS Quantum Dots-G-Quadruplex/Hemin Hybrids as Optical DNA Sensors and Aptasensors. Anal. Chem.82, 7073-7077 (2010).

Freeman, R., Liu, X. & Winner, I. Amplified Multiplexed Analysis of DNA by the Exonuclease III-Catalyzed Regeneration of the Target DNA in the Presence of Functionalized Semiconductor Quantum Dots. Nano Lett.11, 4456-4461 (2011).

Cohen, S. et al.Protein Composition of Catalytically Active Human Telomerase from Immortal Cells. Science.315, 1850-1853 (2007).

Bryan, T. M. &Cech, T. R. Telomerase and the maintenance of chromosome ends. Curr. Opin. Cell Biol.11, 318-324 (1999).

Freeman, R. et al. DNAzyme-Like Activity of Hemin-Telomeric G-Quadruplexes for the Optical Analysis of Telomerase and its Inhibitors. ChemBioChem.1, 2362•2367 (2010).

Freeman, R. et al. Optical Aptasensors for the Analysis of the Vascular Endothelial Growth Factor (VEGF). Anal. Chem.84, 6192-6198 (2012).

Cohen, S. B. & Reddel, R. R. A sensitive direct human telomerase activity assay. Nat. Methods.5, 355-360 (2008).

Kuprys, P. et al. Identification of Telomerase RNAs from Filamentous Fungi Reveals Conservation with Vertebrates and Yeasts. PLoS One. 8, e58661 (2013).

Yin, B. C. et al. One-Step, Multiplexed Fluorescence Detection of microRNAs Based on Duplex-Specific Nuclease Signal Amplification. J Am Chem Soc. 134, 5064-7 (2012).

\* cited by examiner

SEQUENCE LISTING

```
<160> NUMBER OF SEQ ID NOS: 25

<210> SEQ ID NO 1
<211> LENGTH: 11
<212> TYPE: RNA
<213> ORGANISM: Homo sapiens
<220> FEATURE:
<221> NAME/KEY: misc_RNA
<222> LOCATION: (1)..(11)

<400> SEQUENCE: 1
caaucccaau c                                                          11

<210> SEQ ID NO 2
<211> LENGTH: 8
<212> TYPE: RNA
<213> ORGANISM: Tetrahymena thermophila
<220> FEATURE:
<221> NAME/KEY: misc_RNA
<222> LOCATION: (1)..(8)

<400> SEQUENCE: 2 aacccaac                                                               8

<210> SEQ ID NO 3
<211> LENGTH: 16
<212> TYPE: RNA
<213> ORGANISM: Saccharomyces cerevisiae
<220> FEATURE:
<221> NAME/KEY: misc_RNA
<222> LOCATION: (1)..(16)

<400> SEQUENCE: 3
cacacaccca caccac                                                     16

<210> SEQ ID NO 4
<211> LENGTH: 30
<212> TYPE: RNA
<213> ORGANISM: Kluyveromyces lactis
<220> FEATURE:
<221> NAME/KEY: misc_RNA
<222> LOCATION: (1)..(30)
```

-continued

```
<210> SEQ ID NO 5
<211> LENGTH: 7
<212> TYPE: RNA
<213> ORGANISM: Mus musculus
<220> FEATURE:
<221> NAME/KEY: misc_RNA
<222> LOCATION: (1)..(7)

<400> SEQUENCE: 5 uccaauc                                                                        7

<210> SEQ ID NO 6
<211> LENGTH: 6
<212> TYPE: DNA
<213> ORGANISM: Homo sapiens
<220> FEATURE:
<221> NAME/KEY: repeat_unit
<222> LOCATION: (1)..(6)

<400> SEQUENCE: 6 ttaggg                                                                         6

<210> SEQ ID NO 7
<211> LENGTH: 6
<212> TYPE: DNA
<213> ORGANISM: Tetrahymena thermophila
<220> FEATURE:
<221> NAME/KEY: repeat_unit
<222> LOCATION: (1)..(6)

<400> SEQUENCE: 7 ttgggg                                                                         6

<210> SEQ ID NO 8
<211> LENGTH: 5
<212> TYPE: DNA
<213> ORGANISM: Saccharomyces cerevisiae
<220> FEATURE:
<221> NAME/KEY: repeat_unit
<222> LOCATION: (1)..(5)

<400> SEQUENCE: 8 tggtg                                                                          5

<210> SEQ ID NO 9
<211> LENGTH: 7
<212> TYPE: DNA
<213> ORGANISM: Saccharomyces cerevisiae
<220> FEATURE:
<221> NAME/KEY: repeat_unit
<222> LOCATION: (1)..(7)

<400> SEQUENCE: 9 tggtgtg                                                                        7

<210> SEQ ID NO 10
<211> LENGTH: 9
<212> TYPE: DNA
<213> ORGANISM: Saccharomyces cerevisiae
<220> FEATURE:
<221> NAME/KEY: repeat_unit
<222> LOCATION: (1)..(9)
```

Continuation of SEQ ID NO 4:

```
aaacuaaucc auacaccaca ugccuaaacu                                              30
```

```
<400> SEQUENCE: 10 tggtgtgtg                                                                    9

<210> SEQ ID NO 11
<211> LENGTH: 11
<212> TYPE: DNA
<213> ORGANISM: Saccharomyces cerevisiae
<220> FEATURE:
<221> NAME/KEY: repeat_unit
<222> LOCATION: (1)..(11)

<400> SEQUENCE: 11
tggtgtgtgt g                                                                11

<210> SEQ ID NO 12
<211> LENGTH: 13
<212> TYPE: DNA
<213> ORGANISM: Saccharomyces cerevisiae
<220> FEATURE:
<221> NAME/KEY: repeat_unit
<222> LOCATION: (1)..(13)

<400> SEQUENCE: 12
tggtgtgtgt gtg                                                              13

<210> SEQ ID NO 13
<211> LENGTH: 6
<212> TYPE: DNA
<213> ORGANISM: Saccharomyces cerevisiae
<220> FEATURE:
<221> NAME/KEY: repeat_unit
<222> LOCATION: (1)..(6)

<400> SEQUENCE: 13 tgggtg                                                                       6

<210> SEQ ID NO 14
<211> LENGTH: 8
<212> TYPE: DNA
<213> ORGANISM: Saccharomyces cerevisiae
<220> FEATURE:
<221> NAME/KEY: repeat_unit
<222> LOCATION: (1)..(8)

<400> SEQUENCE: 14 tgggtgtg                                                                     8

<210> SEQ ID NO 15
<211> LENGTH: 10
<212> TYPE: DNA
<213> ORGANISM: Saccharomyces cerevisiae
<220> FEATURE:
<221> NAME/KEY: repeat_unit
<222> LOCATION: (1)..(10)

<400> SEQUENCE: 15
tgggtgtgtg                                                                  10

<210> SEQ ID NO 16
<211> LENGTH: 12
<212> TYPE: DNA
<213> ORGANISM: Saccharomyces cerevisiae
<220> FEATURE:
<221> NAME/KEY: repeat_unit
<222> LOCATION: (1)..(12)

<400> SEQUENCE: 16
```

```
tgggtgtgtg tg                                                            12

<210> SEQ ID NO 17
<211> LENGTH: 14
<212> TYPE: DNA
<213> ORGANISM: Saccharomyces cerevisiae
<220> FEATURE:
<221> NAME/KEY: repeat_unit
<222> LOCATION: (1)..(14)

<400> SEQUENCE: 17
tgggtgtgtg tgtg                                                          14

<210> SEQ ID NO 18
<211> LENGTH: 25
<212> TYPE: DNA
<213> ORGANISM: Kluyveromyces lactis
<220> FEATURE:
<221> NAME/KEY: repeat_unit
<222> LOCATION: (1)..(25)

<400> SEQUENCE: 18
acggatttga ttaggtatgt ggtgt                                              25

<210> SEQ ID NO 19
<211> LENGTH: 12
<212> TYPE: DNA
<213> ORGANISM: Aspergillus oryzae
<220> FEATURE:
<221> NAME/KEY: repeat_unit
<222> LOCATION: (1)..(12)

<400> SEQUENCE: 19
ttagggtcaa ca                                                            12

<210> SEQ ID NO 20
<211> LENGTH: 22
<212> TYPE: DNA
<213> ORGANISM: Artificial
<220> FEATURE:
<223> OTHER INFORMATION: complementary sequence for miRNA-141
<220> FEATURE:
<221> NAME/KEY: misc_binding
<222> LOCATION: (1)..(22)

<400> SEQUENCE: 20
ccatctttac cagacagtgt ta                                                 22

<210> SEQ ID NO 21
<211> LENGTH: 22
<212> TYPE: RNA
<213> ORGANISM: Homo sapiens
<220> FEATURE:
<221> NAME/KEY: misc_RNA
<222> LOCATION: (1)..(22)

<400> SEQUENCE: 21
uaacacuguc ugguaaagau gg                                                 22

<210> SEQ ID NO 22
<211> LENGTH: 22
<212> TYPE: RNA
<213> ORGANISM: Homo sapiens
<220> FEATURE:
<221> NAME/KEY: misc_RNA
<222> LOCATION: (1)..(22)
```

```
<400> SEQUENCE: 22
uaauacugcc ugguaaugau ga                                               22

<210> SEQ ID NO 23
<211> LENGTH: 22
<212> TYPE: RNA
<213> ORGANISM: Homo sapiens
<220> FEATURE:
<221> NAME/KEY: misc_RNA
<222> LOCATION: (1)..(22)

<400> SEQUENCE: 23
uaacacuguc ugguaacgau gu                                               22

<210> SEQ ID NO 24
<211> LENGTH: 22
<212> TYPE: RNA
<213> ORGANISM: Homo sapiens
<220> FEATURE:
<221> NAME/KEY: misc_RNA
<222> LOCATION: (1)..(22)

<400> SEQUENCE: 24
uagcuuauca gacugauguu ga                                               22

<210> SEQ ID NO 25
<211> LENGTH: 22
<212> TYPE: RNA
<213> ORGANISM: Homo sapiens
<220> FEATURE:
<221> NAME/KEY: misc_RNA
<222> LOCATION: (1)..(22)

<400> SEQUENCE: 25
ugagguagua gguuguauag uu                                               22
```

KIT COMPRISING A POLYNUCLEOTIDE PROBE FOR DETECTING A TARGET NUCLEIC ACID

BACKGROUND OF THE INVENTION

1. Field of the Invention

The invention relates to a polynucleotide probe for detecting nucleic acid, a method for detecting a target nucleic acid by using the polynucleotide probe and a kit for detecting a target nucleic acid.

2. Description of Related Art

A biomarker is a measurable indicator of a specific biological state, particularly one relevant to the risk of contraction, the presence or the stage of disease. Therefore, the detection and quantification of a suitable biomarker are important for clinical diagnosis, for example, cancer diagnosis.

Prostate cancer (PC) is the most frequently diagnosed cancer, and is a major cause of cancer-related mortality of males. The rapid, reliable and cost effective detection of PC could have a tremendous clinical impact for diagnosis, prognosis, and treatment response. The quantitative analysis of the prostate-specific antigen (PSA) in serum is currently used for diagnosing PC and treatment response. The use of PSA as reliable biomarker for PC was, however, criticized and its diagnostic value was questioned. Elevated amounts of PSA are not specific to the malignant disease, and indolent prostate tumors are false-positively identified as PC. Also, the PSA diagnostic test revealed circa (ca.) 15% of false-negative results. Thus, the development of clinically validated cancer detection markers remains an unmet challenge for many common cancers. New approaches that can complement and improve on current strategies for cancer detection are urgently needed.

MicroRNAs (miRNAs) are small (18-26 nt in size) regulatory RNA molecules that function to modulate the activity of specific mRNA targets and play important roles in a wide range of biological processes, such as cell proliferation or apotosis. More importantly, miRNAs expressions are frequently dysregulated in the development of a variety of cancers. It was further discovered that extracellular miRNAs circulate in the bloodstream and that such circulating miRNAs are remarkably stable, thereby being protected from endogenous RNase activity. Owing to these properties, miRNAs provide a rich platform of biomarkers for different diseases. For example, miRNA-141 (miR-141) was up-regulated in PC specimens, and it was suggested as a potentially useful biomarker for PC.

Recent research efforts are directed toward the application of nanotechnological tools and methods to develop detection platforms for nucleic acids. Among these, different amplified sensing platforms of nucleic acid have employed DNA machineries for the autonomous synthesis of catalytic nucleic acids (DNAzymes) as amplifying labels. Alternatively, the regeneration of the target-analyte caused by biocatalytic transformation using, for example, Exonuclease III and nicking enzymes was used as versatile amplification paths of sensing events. Also, semiconductor quantum dots (QDs) having unique optical property were broadly applied as nanomaterials for developing optical sensing probes. Specifically, QDs were used as readout signals to develop luminescent DNA sensors using fluorescence resonance energy transfer (FRET), chemiluminescence resonance energy transfer (CRET) or electron transfer quenching. Further, the Exonuclease III-catalyzed regeneration of the target DNA with the use of quencher-nucleic acid-functionalized QDs was applied for the amplified, multiplexed, analysis of DNA.

However, to develop more sensitive and specific methods and sensing probes for nucleic acids detection is still a need.

SUMMARY OF THE INVENTION

In one aspect of the present application, a polynucleotide probe for detecting a target nucleic acid that comprises a first sequence; and a second sequence complementary to the target nucleic acid is provided. In one embodiment of the present application, the first sequence comprises a telomerase primer. Preferably, the telomerase primer is at least three continuous nucleotides complementary to a sequence represented by any one of SEQ ID NOs. 1-5. More preferably, the telomerase primer is at least three continuous nucleotides selected from TTAGGG (SEQ ID NO. 6).

In another embodiment of the present application, the second sequence is CCATCTTTACCAGACAGTGTTA (SEQ ID NO. 20).

In another aspect of the present application, the polynucleotide probe is further connected to a support. In one embodiment, the support is a nanoparticle or a bead. Preferably, the nanoparticle comprises one selected from the group consisting of core-type quantum dot, a core-shell quantum dot, an alloyed quantum dot and a combination thereof. More preferably, the nanoparticle is a CdSe/ZnS quantum dot.

In another aspect of the present application, the polynucleotide probe is further connected to an acceptor. Preferably, the acceptor is BHQ2 or Cy5.

In one aspect of the present application, a method for detecting a target nucleic acid is provided and comprises the following steps: providing a sample; contacting the sample with any one of the above-mentioned polynucleotide probes; and adding a nuclease for cleaving the second sequence of the polynucleotide probe.

In one embodiment of the present application, the nuclease is a duplex-specific nuclease.

In another aspect of the present application, the method further comprises the step of adding a nucleic acid synthesis enzyme for providing an extension product. Preferably, the nucleic acid synthesis enzyme is telomerase. In one embodiment, the extension product comprises a nucleotide sequence represented by any one of SEQ ID NOs. 6-19.

In another aspect of the present application, the method further comprises the step of adding a compound for forming a complex with the extension product. Preferably, the compound is an optical active molecule or hemin. The examples of the optical active molecule are thioflavin T and a porphyrin-based molecule, and the examples of the porphyrin-based molecule are protoporphyrin IX (PpIX) and zinc protoporphyrin IX (ZuPpIX).

In one embodiment of the present application, the complex is an optical active molecule-labeled G-quadruplex or a telomeric hemin/G-quadruplex horseradish peroxidase mimicking DNAzyme.

In another aspect of the present application, the method further comprises the step of detecting a signal generated from the complex. In one embodiment, the signal is generated from the complex by adding a reagent that comprises luminal and $H_2O_2$ or comprises 2,2'-azino-bis(3-ethylbenzothiazoline-6-sulphonic acid) (ABTS) and $H_2O_2$.

In one aspect of the present application, a kit for detecting a target nucleic acid is provided and comprises any one of the above-mentioned polynucleotide probes; and a nuclease. Preferably, the nuclease is a duplex-specific nuclease.

In another aspect of the present application, the kit further comprises a nucleic acid synthesis enzyme. Preferably, the nucleic acid synthesis enzyme is telomerase.

In one aspect of the present application, the kit further comprises an optical active molecule or hemin. The examples of the optical active molecule are thioflavin T and a porphyrin-based molecule, and the examples of the porphyrin-based molecule are PpIX and ZnIPpIX.

In another aspect, the kit further comprises a reagent that contains luminal and $H_2O_2$ or contains ABTS and $H_2O_2$.

BRIEF DESCRIPTION OF THE DRAWINGS

FIG. 1A shows a schematic fluorescence analysis of miR-141 by polynucleotide probe (1)(consisting of SEQ ID NO: 6 and SEQ ID NO: 20)-functionalized CdSe/ZnS QDs through DSN-stimulated regeneration of the miR-141 target; FIG. 1B shows time-dependent fluorescence spectra observed upon interacting the polynucleotide probe (1)-modified QDs with miR-141 and DSN (Inset: Fluorescence changes, $\Delta F=F-F_0$, at $\lambda=627$ nm, as a function of time interacting the QDs with miR-141 and DSN); FIG. IC shows fluorescence spectra corresponding to the polynucleotide probe (1)-functionalized QDs system upon analyzing different concentrations of miR-141 using DSN as target regeneration biocatalyst, wherein fluorescence spectra were recorded after a fixed time interval of one hour of reaction (Inset: Derived calibration curve corresponding to the resulting fluorescence change, $\Delta F=F-F_0$, at $\lambda=627$ nm at different concentrations of the target miR-141); and FIG. 1D shows fluorescence changes ($\Delta F=F-F_0$) observed upon interacting the polynucleotide probe (1)-functionalized QDs with different miRs (miR-141 (SEQ ID NO: 21), miR-200b (SEQ ID NO: 22), miR-200a (SEQ ID NO: 23), miR-21 (SEQ ID NO: 24), and let-7a (SEQ ID NO: 25)) and DSN for one hour. (All error bars in the figures indicate standard deviations using N=3 experiments).

FIG. 2A shows a schematic chemiluminescence analysis of miR-141 by the two-step detection platform involving the interaction of the miR-141/polynucleotide probe (1)-modified QDs with DSN and the subsequent telomerization of primer-modified QDs in the presence of telomerase/dNTPs; wherein the quantitative analysis of miR-141 was then transduced by the chemiluminescence generated by the telomeric hemin/G-quadruplex DNAzyme catalyzed oxidation of luminol by $H_2O_2$; FIG. 2B shows time-dependent chemiluminescence spectra generated upon treatment of the polynucleotide probe (1)-functionalized QDs with miR-141 and DSN for a fixed time-interval of one hour and the subsequent interaction of the resulting QDs with telomerase extracted from 5000 PC-3 cells and the dNTPs mixture for variable time-intervals of telomerization (Inset: Chemiluminescence intensities at $\lambda=410$ nm at different time-intervals of telomerization); FIG. 2C shows chemiluminescence spectra obtained upon analyzing miR-141 by applying different concentrations of telomerase for the telomerization process, wherein the polynucleotide probe (1)-modified QDs were subjected to miR-141 and DSN for a fixed time-interval of one hour, the resulting QDs were then interacted with telomerase extracted from different numbers of PC-3 cells and dNTPs, and the telomerization was allowed to proceed for a fixed time interval of four hours (Inset: Chemiluminescence intensities are used as a function of number of PC-3 cells for the telomerization process. At the end of the telomerization, hemin, luminol and $H_2O_2$ were added to the system to generate the chemiluminescence) (The error bars indicate standard deviation of N=3 experiments); FIG. 2D shows chemiluminescence spectra corresponding to the analysis of variable concentrations of miR-141 by the polynucleotide probe (1)-functionalized CdSe/ZnS QDs using the optimized DSN and telomerase/dNTPs conditions as a two-step amplification platform, wherein the polynucleotide probe (1)-modified QDs were reacted with different concentrations of miR-141, treated with DSN and subsequently, with telomerase extracted from 10000 cells and dNTPs mixture for four hours (Inset: Derived calibration curve. Error bars derived from N=3 experiments); and FIG. 2E shows chemiluminescence intensities (expressed as $I_{CL}/I_{CL0}$, where $I_{CL}$ and $I_{CL0}$ represent the chemiluminescence generated in the presence and absence of the miR, respectively) generated upon analysis of different miRs (miR-141 (SEQ ID NO. 21), miR-200b (SEQ ID NO: 22), miR-200a (SEQ ID NO: 23), miR-21 (SEQ ID NO: 24), and let-7a (SEQ ID NO: 25)), using the polynucleotide probe (1)-functionalized QDs and the DSN/telomerase analysis scheme.

DETAILED DESCRIPTION OF THE PREFERRED EMBODIMENTS

Figure 1A:
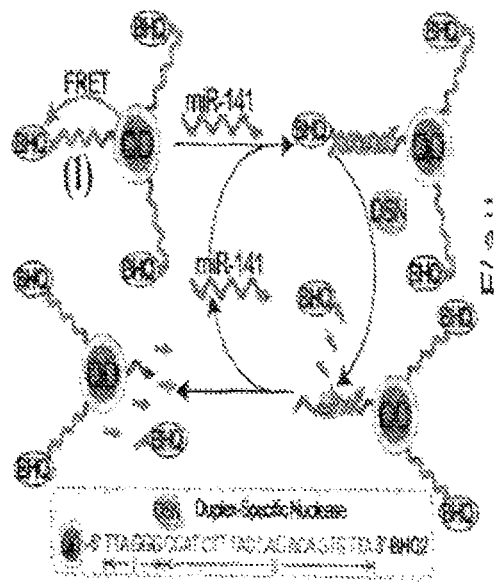
FIGS. 1A-1D show an amplified detection of miR-141 through duplex-specific nuclease (DSN)-stimulated cleavage of the miR-141 target.

The following specific examples are used for illustrating the present invention. A person skilled in the art can easily conceive the other advantages and effects of the present invention. The present invention can also be implemented by different specific cases be enacted or application, the details of the instructions can also be based on different perspectives and applications in various modifications and changes do not depart from the spirit of the creation.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The term "telomerase primer" used herein refers to a nucleotide fragment that can be identified by a telomerase and can be selected based on a telomerase RNA template. The telomerase primer does not need to be completely complementary to the telomerase RNA template and can be a nucleotide fragment complementary to at least any three continuous nucleotides of the telomerase RNA template. The examples of the telomerase RNA template are shown in the following Table 1 (referring to Paulius Kuprys;

Eukaryon Journal; March, 2013; Identification of the First Telomerase RNA from the Filamentous Fungus *Aspergillus oryzae* and Related Organisms). As an example, in light of the following telomerase RNA templates, the telomerase primer can be, but is not limited to, TTA, GGG or GTT.

TABLE 1

Examples of telomerase RNA template

| Organism | Telomerase RNA template (3'->5') | Telomeric repeat (5'->3') |
|---|---|---|
| Homo sapiens | CAAUCCCAAUC (SEQ ID NO. 1) | TTAGGG (SEQ ID NO. 6) |
| Tetrahymena thermophila | AACCCAAC (SEQ ID NO. 2) | TTGGGG (SEQ ID NO. 7) |
| Saccharomyces cerevisiae | CACACACCCACACCAC (SEQ ID NO. 3) | $T(G)_{2-3}(TG)_{1-5}$ (SEQ ID NOs. 8-17) |
| Kluyveromyces lactis | AAACUAAUCCAUACACCACAUG CCUAAACU (SEQ ID NO. 4) | ACGGATTTGATTAGGTATGTGGTG T (SEQ ID NO. 18) |
| Mus musculus | UCCAAUC (SEQ ID NO. 5) | TTAGGG (SEQ ID NO. 6) |
| Aspergillus oryzae | unkown | TTAGGGTCAACA (SEQ ID NO. 19) |

The polynucleotide probe used in the method of the present invention comprises a first sequence and a second sequence complementary to the target nucleic acid. As used herein, the term "first sequence" can be a primer which can serve as a starting point for a DNA synthesis. In the DNA synthesis, the nucleic acid synthesis enzyme is involved, and it can bind to the primer to synthesis a DNA extension product. The nucleic acid synthesis enzyme binding to the first sequence of the polynucleotide probe can be any suitable nucleic acid synthesis enzymes. The nucleic acid synthesis enzyme used in the method of the present invention is not particularly limited and can be appropriately selected according to the purpose. It is preferred that the first sequence of the polynucleotide probe comprises a telomerase primer which can bind to telomerase as a nucleic acid synthesis enzyme.

Telomerase is a ribonucleoprotein that includes a nucleic acid template in the protein backbone. It is over-expressed in cancer cells and it catalyzes the extension of the telomerase primer, in the presence of the dNTPs bases, to form the telomere chains consisting of the telomeric repeat units.

In the telomere chains, the sequences of telomeric repeat units vary with organisms based on slightly different sequences of telomerase templates as shown in Table 1. Since the resulting telomere chains are rich in guanine, such chains self-assemble into a four-stranded structure, i.e., G-quadruplexes.

It is preferred that the first sequence of the polynucleotide probe used in the present invention comprises a telomerase primer that is at least three continuous nucleotides complementary to a sequence represented by any one of SEQ ID NOs. 1-5. In one embodiment, the first sequence comprises at least three continuous nucleotides selected from TTAGGG. In another embodiment, the first sequence comprises TTAGGG. It is preferred that the extension product provided by the nucleic acid synthesis enzyme binding to the first sequence comprises a telomeric repeat unit represented by any one of SEQ ID NOs. 6-19.

As used herein, the term "second sequence" means a nucleotide sequence capable of complementing to the target nucleic acid. It is preferred that the target nucleic acid may be a biomarker which serves as a distinctive biological or biologically derived indicator of a process, event, or condition (such as aging, disease, or exposure to a toxic substance). For example, the target nucleic acid is a miRNA as a biomarker for cancer diagnosis. In one embodiment, the second sequence of the polynucleotide probe used in the present invention comprises a sequence complementary to miR-141 (5'-UAACACUGUCUGGUAAAGAUGG-3') (SEQ ID NO. 21), i.e., 5'-CCATCTTTACCAGACAGT-GTTA-3' (SEQ ID NO. 20).

The polynucleotide probe used in the method of the present invention may be connected to a support. The examples of the support include a nanoparticle and a bead. The nanoparticle may have an optical property, that is, it can absorb light and/or emit light. The examples of the nanoparticle may be, but are not limited to, a quantum dot. The term "quantum dot" generally refers to semiconductor or metal nanoparticles that absorb light and quickly re-emit light in a different color depending on the size of the dot. There are three general types of quantum dot: core-type quantum dots, such as CdSe, CdTe, CdS and CdS-6; core-shell quantum dots, such as CdSe/ZnS, CdTe/CdSe, CdTe/CdS, CdSe/ZnTe, InP/ZnS and InP/GaAs; and alloyed quantum dots, such as CdSeS/ZnS. In one embodiment, the nanoparticle is a CdSe/ZnS quantum dot.

The polynucleotide probe used in the method of the present invention may further be connected to an acceptor. As used herein, the term "acceptor" means a molecule that can accept the luminescence from the nanoparticles having an optical property. Specifically, the nanoparticles (a donor chromophore, such as ODs) may transfer energy to the acceptor, thus triggering-on the luminescence changes. The acceptor may be, but is not limited to, a fluorescent dye such as Cy5, or a quencher such as black-hole quencher (BHQ2). For example, when the acceptor is a fluorescent dye, as the fluorescence resonance energy transfer (FRET) process is enhanced, resulting in the decrease in the luminescence of the nanoparticles and the enhanced fluorescence of the dye; and when the acceptor is a quencher, the luminescence of the nanoparticles is turned-off through the FRET quenching by the quencher. In one embodiment, the acceptor is BHQ2.

As used herein, the term "nuclease" means an enzyme capable of cleaving the phosphodiester bonds between the nucleotides. Nucleases are generally divided into endonuclease and exonuclease, and the examples of well known nucleases are deoxyribonuclease and ribonuclease. The nuclease used in the method of the present invention is not particularly limited and can be appropriately selected according to the purpose. The nuclease is used for cleaving the second sequence of the polynucleotide probe. In one embodiment, the nuclease is a duplex-specific nuclease (DSN), which displays a strong preference for cleaving double-stranded DNA and DNA in DNA-RNA hybrid duplexes, compared to single-stranded DNA.

As used herein, the term "compound" refers to any molecules that are capable of binding to the extension product provided by the nucleic acid synthesis enzyme, so as to form a complex. The complex formed by the compound and the extension product is capable of generating a signal, such that it can be used as a reporter. The examples of the compound may be, but are not limited to, an optical active molecule or hemin. The optical active molecule includes a fluorescent chemical compound that can re-emit light upon light excitation. The known fluorescent chemical compounds are, for example, thioflavin T and a porphyrin-based molecule such as protoporphyrin IX (PpIX) or zinc protoporphyrin IX (ZnPpIX). It is preferred that the optical active molecule are incorporated into the four-stranded structure of the extension product (e.g., G-quadruplex), such that the signal generated from the optical active molecule-labeled complex is enhanced. In another embodiment, the compound is hemin. In the presence of hemin, the four-stranded structure of the extension product may yield a telomeric hemin/G-quadruplex horseradish peroxidase mimicking DNAzyme unit. The unit is found to catalyze the oxidation of luminol by $H_2O_2$, so as to generate chemiluminescence. In the method of the present invention, the complex formed by the compound and the extension product can produce a signal such as different intensity of color signals, light absorption value or fluorescent signal that can achieve a target nucleic acid quantitative detection.

The means for detecting the signal is well known in the art. The detection means is not particularly limited and can be appropriately selected according to the purpose. For example, when the signal is emission, quenching, etc., it is detected by a photodetector, camera, and so on.

Many examples have been used to illustrate the present invention. The examples below should not be taken as a limit to the scope of the invention.

EXAMPLES

Chemicals and Reagents

NaCl (sodium chloride), $MgCl_2$ (magnesium chloride), KCl (potassium chloride), NaOH (sodium hydroxide), $CHCl_3$ (chloroform), $K_2HPO_4$ (potassium phosphate dibasic), $KH_2PO_4$ (potassium phosphate monobasic), 35% HCl (hydrochloric acid), 35% $H_2O_2$ (hydrogen peroxide), HEPES (4-(2-hydroxyethyl)piperazine-1-ethanesulfonic acid), DMSO (dimethyl sulfoxide), PMSF (phenylmethanesulfonyl fluoride), DTT ($_{DL}$-dithiothreitol), GSH ($_L$-gutathione reduced), MeOH (methanol), Tris-HCl (trizma hydrochloride), hemin, spermidine, glycerol, and luminol were purchased from Sigma-Aldrich (St. Louis, Mo., USA). Triton-X100 (iso-octylphenoxypolyethoxyethanol) was obtained from ThermoFisher Scientific (MA, USA). EDTA (ethylene diaminetetra acetate) was acquired from Amersham Pharmacia Biotech (St. Albans, UK). $BS^3$ (bis[sulfosuccinimidyl]suberate) was obtained from Pierce Biotechnology (Rockford, Ill., USA). CdSe/ZnS QD (10 mg/mL) in toluene were purchased from NN-LABS (LLC., Fayetteville, Ark.). Duplex-specific nuclease (DSN) was acquired from Evrogen Joint Stock company (Moscow, Russia). RNase inhibitor and dNTP were purchased from Roche (Indianapolis, Ind., USA). Human miRNeasy serum/plasma kit (Cat. No. 217184) was obtained from Qiagen (Valencia, Calif.). Human prostate-specific antigen ELISA kit (Cat. No. 55R-BC2601) was obtained from Fitzgerald Industries International (MA, USA). All aqueous solutions were prepared using distilled and deionized water (d.d. water, resistivity >18 MΩ·cm) purified with a Milli-Q water purification system (Bedford, Mass.). All pipette tips and tubes are RNase-free and used without further RNase inactivation. All glassware was oven baked at 250° C. for 4 hr before use to inactivate any RNase. Oligonucleotides were purchased from Integrated DNA Technologies (Coralville, Iowa). All oligonucleotides were used as provided and diluted with, 10 mM of phosphate buffer solution (pH 7) to obtain stock solution of 100 µM.

Example 1. Preparation of Polynucleotide Probe Modified with GSH-Functionalized CdSe/ZnS Quantum Dots A GSH-functionalized quantum dots (GSH-QDs) were prepared based on the modified ligand exchange procedure as follows. The functionalization was initiated by transferring the QDs from toluene to $CHCl_3$. First, 20 µL of CdSe/ZnS core/shell octadecylamine (ODA)-capped QDs were precipitated from the stock solution upon addition of 0.8 mL of MeOH. Followed by centrifugation at 3000 rpm for 5 min, the toluene supernatant was decanted and the resulting precipitate was re-suspended in 0.4 mL of $CHCl_3$. To substitute ODA ligand for GSH ligand, 1 mL of GSH alkaline methanol solution (40 mg/mL in MeOH containing KOH, 20 mg/mL) was slowly added to the QDs solution (in $CHCl_3$) at ambient temperature. The above mixture was reacted at 50° C. for 2 hr and subsequently cooled down to 27° C. and allowed to react overnight. After an addition of 1 mL of 1 mM NaOH aqueous solution, GSH-decorated QDs were partitioned to the upper aqueous phase, indicating the successful exchange of ligand. Finally, methanol was added to the aqueous phase containing GSH-functionalized QDs, followed by centrifugation at 3000 rpm for 3 min to remove unreacted GSH. The purified GSH-functionalized QDs thereafter were re-suspended in 200 µL of double-distilled water and stored at 4° C. prior to use.

To prepare a polynucleotide probe modified with GSH-functionalized QDs, the GSH-functionalized QDs were first reacted with $BS^3$ in HEPES buffer (100 mM, pH 7) for 20 min at ambient temperature, followed by the precipitation with the addition of 200 µL of MeOH and 3 mg of NaCl to remove the excess of free $BS^3$. To the resulting purified QDs, 50 µL of the polynucleotide probe (1) (10 mM, in phosphate buffer, pH 7) was added. The reaction mixture was shaken for 2 hr and the purification steps using MeOH and NaCl as described above were repeated twice. The polynucleotide probe (1)-modified QDs were re-suspended in 200 µL of HEPES buffer (100 mM, pH 7) and stored at 4° C. before use.

The polynucleotide probe (1) was represented by SEQ ID NO: 21 (5'-TTAGGGCCATCTTTACCAGACAGTGTTA-3') and connected to BHQ2 quencher at its 3'-end, wherein SEQ ID NO: 21 includes a first sequence comprising telomerase primer of TTAGGG (SEQ ID NO: 6), and a second sequence represented by SEQ ID NO: 20, which is complementary to miR-141.

To determine the loading of the GSH-functionalized QDs with the polynucleotide probe, the absorption spectrum of a known concentration of non-modified QDs (GSH-functionalized QDs) was recorded prior to the modification of the QDs with the polynucleotide probe. Normalization was then carried out to the same OD value at λ=620 nm recorded for the non-modified QDs since DNA does not absorb light at 620 nm. The subtraction of the spectrum of modified QDs from the non-modified QDs yields the absorbance difference at λ=620 nm, which allows the calculation of the polynucleotide probe concentration. Knowing the concentration of QDs and the concentration of the polynucleotide probe, the loading of the polynucleotide on the QDs was evaluated using a Cary 300 Bio UV-VIS spectrophotometer (Varian, Mulgrave Victoria, Australia).

The average coverage of the polynucleotide probe (1) on the QDs was determined spectroscopically to be 8 units per particle.

Example 2. Preparation of Telomerase Extract

PC-3 cells cultured in Ham's F12K medium with 10% fetal bovine serum (FBS) and 1% penicillin-streptomycin were obtained from the Culture Collection and Research Center (CCRC) (Hsinchu, Taiwan). The cells were grown with fresh medium on a 75 cm$^2$ flask at 37° C. in a humidified 5% $CO_2$ incubator. After harvested with trypsin, cells were centrifuged at 5000 rpm for 5 min to remove medium. The telomerase in the resulting PC-3 cell pellet was extracted according to the protocol reported by Cohen and Reddel, *Nat. Methods* 5, 355-360 (2008).

Example 3. Isolation of MicroRNA from Clinical Samples

All serum samples of prostate cancer carriers and healthy individuals were collected by the team of Dr. Yen-Chuan Ou at Division of Urology, Taichung Veterans General Hospital. All samples analyzed in the current study were appropriately consented and collected using IRB approved clinical protocols from donors with prostate cancer and matched. Circulating microRNA in sera was extracted using the human miRNeasy serum/plasma kit according to the manufacturer's instruction as follows. 1 mL of Qiazol lysis reagent and 20 U of RNase inhibitor were added to 0.2 mL of serum and mixed by pipetting, followed by incubation at ambient temperature for 5 min to dissociate nucleoprotein complexes. After adding 0.2 mL of $CHCl_3$, the mixture was vigorously vortexed for 15 s and incubated at room temperature for 3 min, followed by centrifugation at 12000 g at 4° C. for 15 min. The upper aqueous phase containing microRNA was obtained, to which 1.5 volumes of 95% EtOH was added and mixed by pipetting again. Finally, purification of microRNA was carried out using a spin-column format as described in the protocol. The purified microRNA extracted from each clinical serum sample was eluted with double-distilled water (14 µL) and stored at −20° C. before analysis.

Example 4. Analysis of miR-141 by the Fluorescence Method

The fluorescence approach for the analysis of miR-141 was performed by preparing mixture consisting of 30 µL of DSN (0.2 U), polynucleotide probe (1)-modified QDs (33.3 nmol) and the target microRNA (5 µL of the specified concentration) in 50 mM of Tris-HCl buffer solution containing 5 mM $MgCl_2$ and 1 mM DTT, pH 8, followed by the incubation at 55° C. for 1 hr. The reaction volume was brought up to 100 µL with the same buffer solution and the fluorescence changes were recorded using a Varian Cary Eclipse fluorescence spectrometer (Varian, Mulgrave Victoria, Australia).

Referring to FIG. 1A, GHS-functionalized CdSe/ZnS QDs were reacted with the 5'-amino functionalized polynucleotide probe (1) modified at its 3'-end with the BHQ2 quencher. In the presence of miR-141, the duplex between miR-141 and the second sequence of polynucleotide probe (1) is formed. Subjecting the system to DSN, the 3'-end of the duplex polynucleotide probe (1)/miR-141 was cleaved off, resulting in the removal of the BHQ-quencher, the sequential degradation of the duplex second sequence of polynucleotide probe (1), and the recycling of the miR-141 that bound to another polynucleotide probe (1) modified with the QDs. The DSN-stimulated cleavage of the polynucleotide probe (1) strands leaded to the removal of the quencher units and to the switching "on" of the luminescence of the QDs. The sequential recycling of the target miR-141 by the DSN-mediated process provides an amplification path for the sensing process.

Besides, the DSN-mediated digestion of the second sequence of polynucleotide probe (1) resulted in a short nucleic acid single-stranded tether that was a part of the first sequence connected to the QDs, and was unaffected by DSN.

Figure 1B:
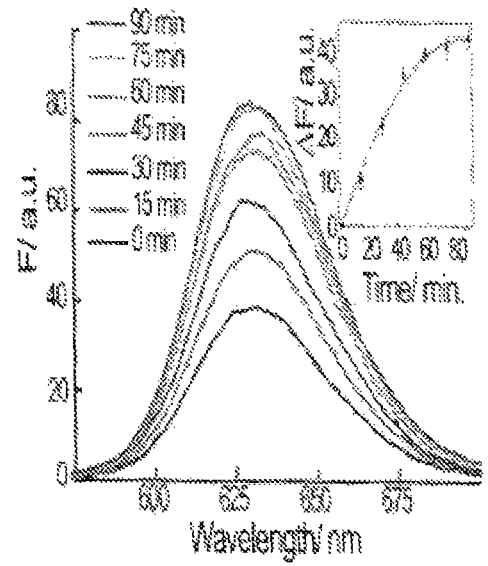

Referring to FIG. 1B, it shows the time-dependent luminescence changes upon subjecting the polynucleotide probe (1)-modified QDs to miR-141, $1 \times 10^{-7}$ M, in the presence of DSN. The luminescence of the QDs increased with time and it reached a saturation value after ca. 60 min. The time-dependent fluorescence changes corresponded to the dynamics of the DSN-induced regeneration of the target miR-141 and the cleavage of the quencher associated with the QDs.

Figure 1C:
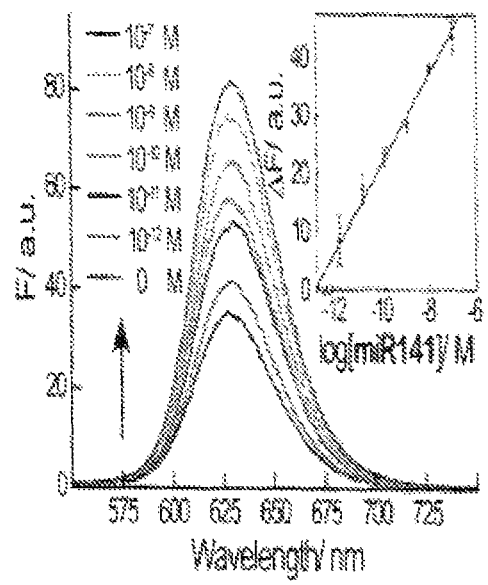

Referring to FIG. 1C, it shows the luminescence spectra recorded upon subjecting the polynucleotide probe (1)-modified QDs with variable concentrations of miR-141, in the presence of DSN, for a fixed time-interval. As the concentration of miR-141 increased, the fluorescence was intensified, consistent with the higher degree of cleaved-off quencher. In addition, as the calibration curve shown in FIG. 1C, the system allowed the analysis of miR-141 with a detection limit of $1.7 \times 10^{-12}$ M.

Example 5. Comparison Between miR-141 and Other Homologous MicroRNAs by the Fluorescence Method The selectivity toward the sensing of miR-141 is, however, an important issue, since other miRNAs include homologous nucleotide domains to the miR-141, and hence might interfere with the specific analysis of miR-141. Accordingly, the fluorescence responses of the polynucleotide probe (1)-modified QDs to miR-200a, miR-200b, miR-21, and let-7a were examined.

The examination method was analogous to the above miR-141 analysis except that the target microRNA was replaced with such homologous miRNAs, which have the following sequences:

```
miR-200b:
                                    SEQ ID NO: 22
(5'-UAAUACUGCCUGGUAAUGAUGA-3')

miR-200a:
                                    SEQ ID NO: 23
(5'-UAACACUGUCUGGUAACGAUGU-3')
```

-continued miR-21:
SEQ ID NO: 24
(5'-UAGCUUAUCAGACUGAUGUUGA-3')

let-7a:
SEQ ID NO: 25
(5'-UGAGGUAGUAGGUUGUAUAGUU-3')

Figure 1D:
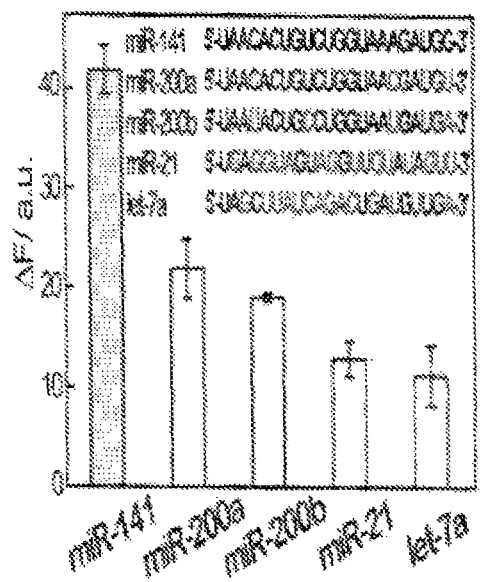

Referring to FIG. 1D, miR-200a and 200b, which have high sequence identity with miR-141, exhibited significant differences in the fluorescence signals compared to miR-141 (52% and 46% of the miR-141 signal, respectively). The result was consistent with the fact that these miRs hybridize with polynucleotide probe (1) leading to their partial cleavage by DSN. While the relative concentrations of miR-200a and miR-200b as compared to miR-141 in real biological samples are unknown, their fluorescence response might, indeed, perturb the quantitative measurement of miR-141.

Example 6. Analysis of MicroRNAs by the Chemiluminescence Method

To overcome the selectivity limitation upon the one-step detection of miR-141, and to amplify the primary recognition event of miR-141, the telomerase as catalytic amplifier was applied. In this example, the catalytic properties of the telomeric hemin/G-quadruplex products and the chemiluminescence approach were harnessed to amplify and to enhance the selectivity of the detection of miR-141 on the QDs support.

The chemiluminescence approach for the analysis of miR-141 was performed by preparing a 30 μL of mixture solution consisting of DSN (0.2 U), polynucleotide probe (1)-modified QDs (33.3 nmol) and the target microRNA (5 μL of the specified concentration) in 50 mM of Tris-HCl buffer solution containing 5 mM $MgCl_2$ and 1 mM DTT, pH 8, was incubated at 55° C. for 1 hr. The telomerization reaction was initiated by adding 20 μL of dNTPs mixture containing 0.2 mM each of dNTP, telomerase (extracted from $10^4$ PC-3 cells), 300 mM KCl, and 1 mM spermidine was added to the QDs mixture and such system was allowed to react at 37° C. for 4 hr. After telomerization, the resulting mixture was treated with 1 μL of 0.05 mM hemin for another 30 min at ambient temperature. Subsequently, 25 μL of luminol (5 mM) and 25 μL of $H_2O_2$ (300 mM) were quickly added. The chemiluminescence emission intensity was measured immediately using a photon-counting spectrometer (Edinburgh Instruments, F900).

Figure 2A:
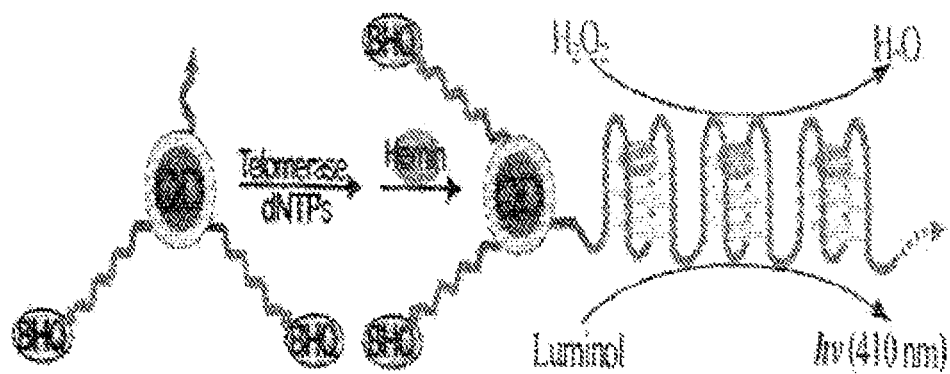
FIGS. 2A-2E show a two-step amplified detection of miR-141 through the telomerase-stimulated telomerization of the first sequence as primer associated with the QDs.

Referring to FIG. 2A, the DSN-stimulated cleavage of the duplex miR-141/second sequence of the polynucleotide probe (I) resulted in the hydrolytic digestion of second sequence and the regeneration of miR-141, while the first sequence tethered to the QDs corresponded to the primer sequence of telomerase. Accordingly, the QDs functionalized with first sequence were treated with telomerase extracted from PC-3 cells in the presence of the dNTPs mixture.

This resulted in the telomerization of the first sequence and, in the presence of hemin, the self-assembly of the catalytic-telomeric hemin/G-quadruplexes that generated chemiluminescence as readout for miR-141.

Figure 2B:
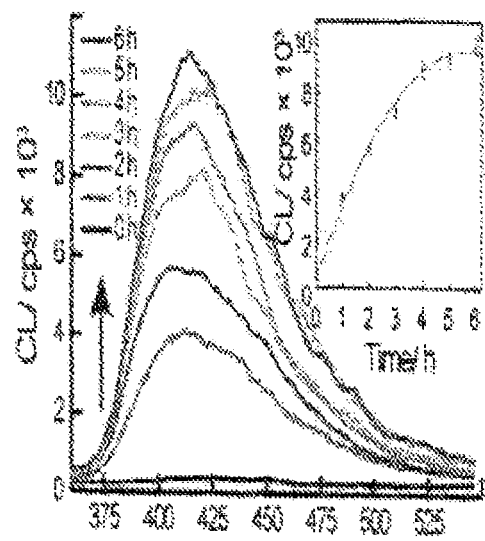

Referring to FIG. 2B, it shows the time-dependent chemiluminescence spectra observed upon the treatment of the polynucleotide probe (1)-functionalized QDs with a fixed concentration of miR-141 ($1 \times 10^{-7}$ M) and the DSN, for a fixed time interval (60 minutes), and subsequently interacted with telomerase and dNTPs for variable time intervals. As the reaction time was prolonged, the chemiluminescence was intensified, consistent with the formation of more hemin/G-quadruplexes. In addition, as the time-dependent chemiluminescence intensities shown in the inset of FIG. 2B, the chemiluminescence intensities leveled off to a saturation value after ca. four hours of telomerization.

Figure 2C:
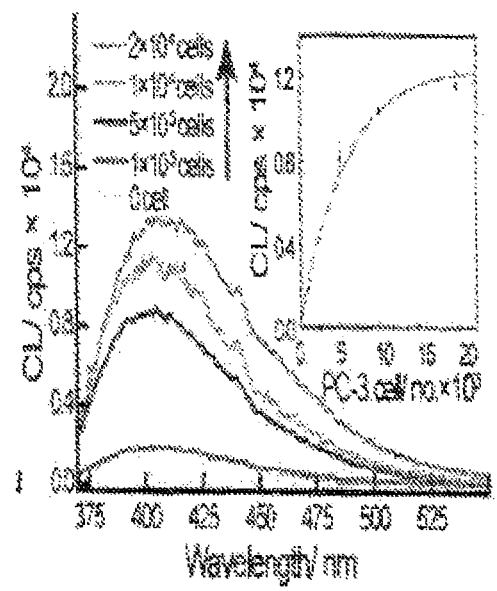

Referring to FIG. 2C, it shows the chemiluminescence spectra generated by the miR-141/DSN-treated QDs that were interacted with telomerase extracted from variable numbers of cells in the presence of the dNTPs mixture for a fixed time interval of four hours. As the telomerase content increased, the resulting chemiluminescence was intensified, consistent with the higher content of synthesized hemin/G-quadruplex catalytic units. In addition, the inset of FIG. 2C shows the resulting calibration curve corresponding to the chemiluminescence intensities generated by telomerase extracted from different number of cells. The chemiluminescence intensities leveled off to a saturation value upon using telomerase extracted from 10,000 cells.

Figure 2D:
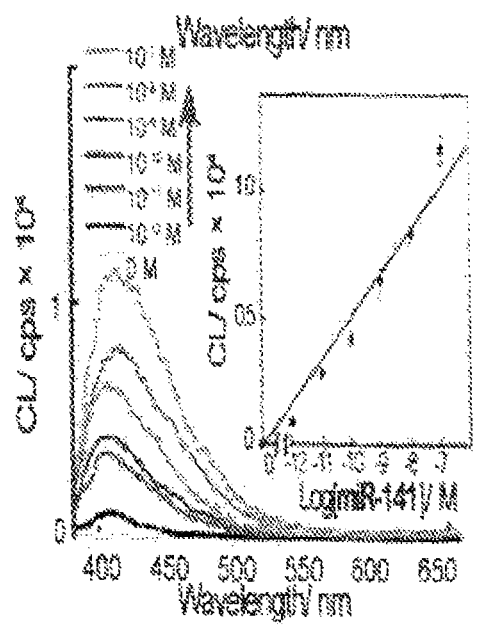

Referring to FIG. 2D, it shows the optimization of the different steps to analyze miR-141 by the primary DSN-stimulated regeneration of the miR-141, and the secondary amplified telomerization process enabled the sequential analysis of variable concentrations of miR-141. As the concentration of miR-141 increased, the resulting chemiluminescence was intensified, consistent with the enhanced generation of the telomeric DNAzyme. In addition, the inset of FIG. 2D shows the calibration curve corresponding to the chemiluminescence intensities generated upon analyzing variable concentrations of miR-141 by the coupled DSN/telomerase platform. The detection limit for analyzing miR-141 corresponded to $2.8 \times 10^{-13}$ M.

Figure 2E:
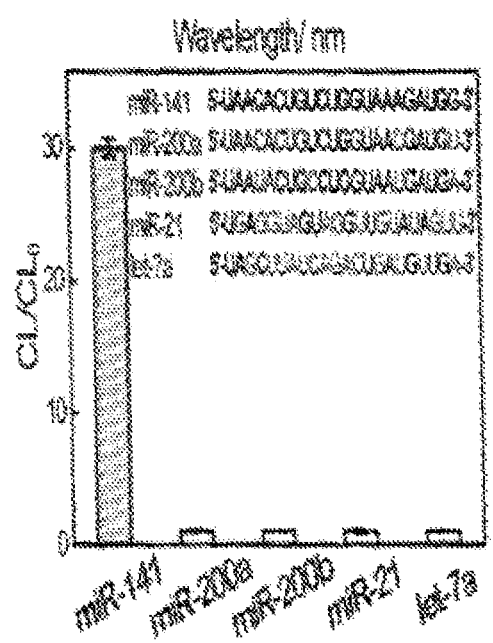

Referring to FIG. 2E, the most interesting result is, however, the impressive selectivity in the telomerase-stimulated chemiluminescence detection of miR-141. Apparently, the functional QDs subjected to miRNAs other than miR-141 did not show any chemiluminescence signal.

It could be seen that despite the high sequence identity, miR-200a and miR-200b included several base mismatches and their 3'-ends were particularly non-complementary to the polynucleotide probe (1). The incomplete complementarity of the different miRs to the polynucleotide probe (1) leads, in the presence of DSN, to perturbed first sequence that included overhangs not recognized by telomerase. Consequently, this impressive selectivity was due to the fact that the DSN cleavage of foreign miRNA/polynucleotide probe (1) duplexes does not yield the free first sequence that was generated in the presence of miR-141. Thus, the foreign miRNA could not initiate the telomerization, implying that the secondary telomerase-stimulated elongation of the tether of first sequence associated with the QDs was prohibited. That is, the selectively to the miR-141/DSN-generated sequence was achieved.

Example 7. Analysis of Human Prostate-Specific Antigen (PSA) in Clinical Sera Samples For comparing the polynucleotide probe-based sensing platforms for the detection of the miR-141 biomarker with the commercial ELISA kit for the analysis of the PSA, the polynucleotide probe-based sensing platform and the commercial ELISA kit were applied for detecting the biomarker in the same serum samples.

The analysis of human PSA in clinical serum samples was performed using a commercial ELISA kit according to manufacturer's instruction. Specifically, the commercial ELISA kit involved horseradish peroxidase-labeled antibodies as catalysts for the generation of a colorimetric signal via the $H_2O_2$ stimulated oxidation of Tetramethylbenzidine (TMB) to the colored benzidine, TMBox. The absorbance changes at 450 nm were measured by a 96-well microplate reader (Sunrise, Tecan Trading AG, Switzerland).

Figure 3:
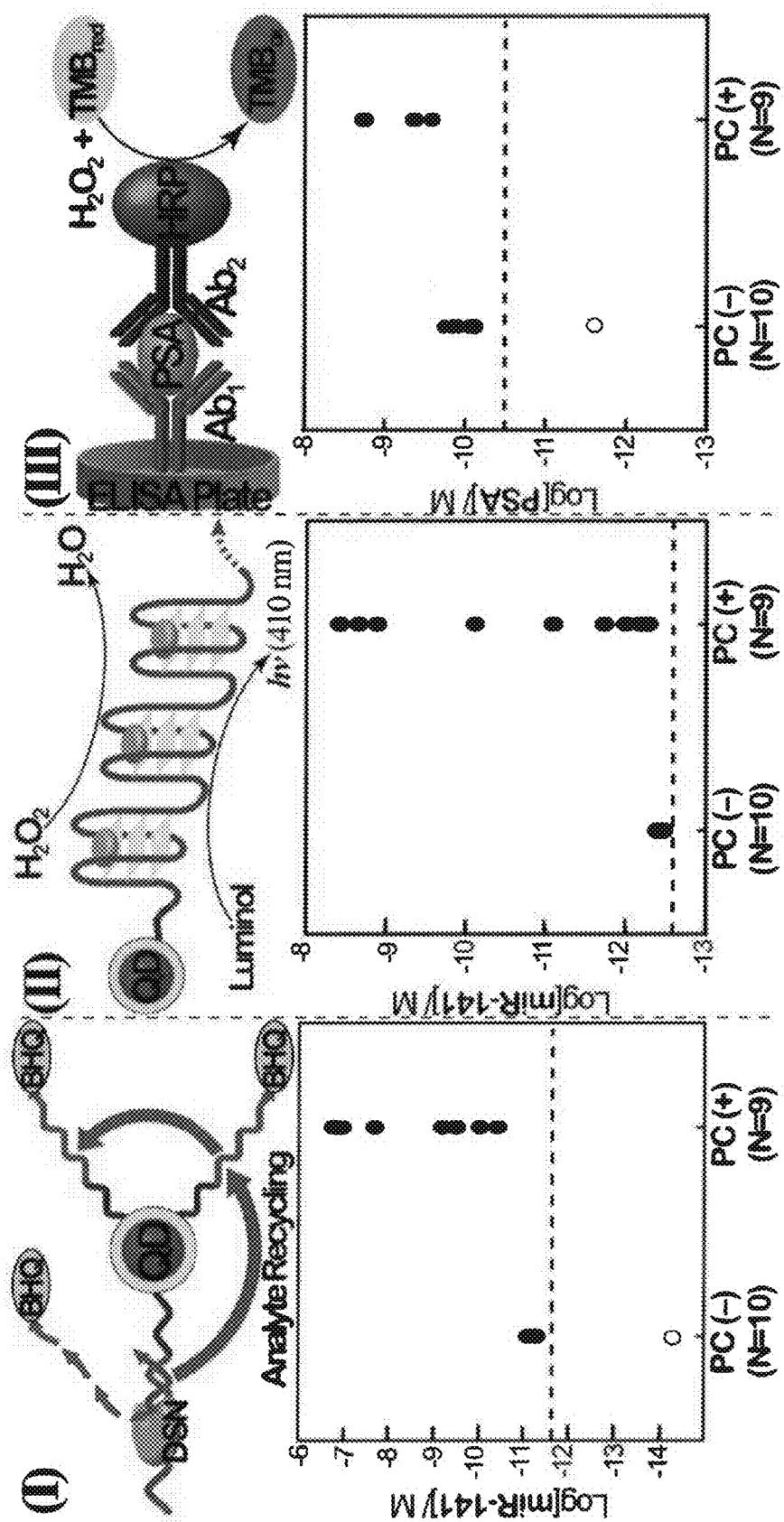
FIG. 3 shows comparison of the analysis of miR-141 and PSA in human clinical samples using the QD/telomerase assays and PSA/ELISA immunoassay. Scatter plots corresponding to the analysis of sera samples of healthy individuals (PC (−), prostate cancer negative), N=10, and prostate cancer carriers (PC (+), prostate cancer positive), N=9. Panel I: Concentrations of miR-141 evaluated by the DSN-stimulated cleavage of the polynucleotide probe (1)-functionalized QDs. Panel II: Concentrations of miR-141 in the samples evaluated by the chemiluminescence generated by the two-step DSN/telomerase-dNTPs analysis platform. Panel III: Concentrations of PSA evaluated by the standard immunoassay. Horizontal dotted line represents the corresponding detection limit for each assay. Open circle represents value<LOD (N=7 in panel I; N=3 in panel III).

Human serum samples of PC carriers and healthy individuals were analyzed. Referring to FIG. 3, it shows the scatter plots corresponding to three detection methods: the polynucleotide probe (1)-modified QDs for the one-step fluorescence detection of miR-141 (panel I); the two-step telomerase-stimulated chemiluminescence analysis of miR-141 by the polynucleotide probe (1)-modified QDs (panel II); and the commercial ELISA kit for the analysis of the PSA (panel III).

Using the calibration curves for the analysis of miR-141 by the polynucleotide probe (1)-modified QDs according to the inset of FIG. 1C, and by the telomerase-stimulated chemiluminescence readout according to FIG. 2D, the scatter plots for the "quantitative" analysis of miR-141 in the serum samples are presented in panels I and II of FIG. 3, respectively. The results revealed several important features and even apparent discrepancies: (a) both methods revealed distinct and distinguishable concentration regions for the fluorescence or chemiluminescence intensities associated with healthy individuals or PC carriers; (b) There was an apparent discrepancy in the concentrations of miR-141 evaluated by the fluorescence QDs or the chemiluminescence readout methods. The fluorescence generated by the QDs required higher concentrations of miR-141 as compared to the concentrations of miR-141 detected by the chemiluminescence method, in the samples of the PC carriers. While the one-step fluorescence detection method indicated miR-141 concentrations in the range of $3.8 \times 10^{-11}$ M to $1.7 \times 10^{-7}$ M, the same samples analyzed by the two-step chemiluminescence method revealed a ca. 70-fold lower concentrations range of miR-141, $5.3 \times 10^{-13}$ M to $3.9 \times 10^{-9}$ M; (c) The scatter plot corresponding to the chemiluminescence intensities generated by healthy individuals converges into a single value of $(4 \pm 0.2) \times 10^{-13}$ M.

The present invention has finds a new sensing platform for detecting a target nucleic acid, particularly for the cancer biomarker. In view of the controversy existing in the implementation of the PSA immunoassay for prognosis or validating PC, the method according to the present invention is useful to be a substitute analytical test.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claim.

The references listed below cited in the application are each incorporated by reference as if they were incorporated individually.

1. Jemal, A., Siegel, R., Xu, J. & Ward, E. Cancer Statistics. *Cancer J. Clin.* 60, 277-300 (2010).
2, Schröder; F. H. & Roobol, M. J. Defining the optimal prostate-specific antigen threshold for the diagnosis of prostate cancer. *Curr. Opin. Urol.* 19, 227-231 (2009).
3. Kirsten L., G. et al. Valodation of the Kattan Preoperative Nomogram for Prostate Cancer Recurrence Using a Community Based Cohort: Results from Cancer of the Prostate Strategic Urological Research Endeavor (capsure). *J. Urol.* 171, 2255-2259 (2004).
4. Catto, J. W. F. et al. Distinct MicroRNA Alterations Characterize High and Low-Grade Bladder Cancer. *Cancer Res.* 69, 8472-8481 (2009).
5. Blenkiron, C. et al. MicroRNA expression profiling of human breast cancer identifies new markers of tumor subtype. *Genome Biol.* 8, R214 (2007).
6. Mitchell, P. S. et al. Circulating microRNAs as stable blood-based markers for cancer detection. *Proc. Nat. Acad. Sci. U.S.A.* 105, 10513-10518 (2008).
7. Liu, S. et al. Enzyme-free and ultrasensitive electrochemical detection of nucleic acids by target catalyzed hairpin assembly followed with hybridization chain reaction. *Biosens. Bioelectron.* 49, 472-477 (2013).
8. Shimron, S., Wang, F., Orbah, R. & Willner I. Amplified Detection of DNA through the Enzyme-Free Autonomous Assembly of Hemin/G-Quadruplex DNAzyme Nanowires. *Anal. Chem.* 84, 1042-1048 (2012).
9. Wang, F., Elbaz, J., Orbah, R., Megan, N. & Willner, I. Amplified Analysis of DNA by the Autonomous Assembly of Polymers Consisting of DNAzyme Wires. *J. Am. Chem. Soc.* 133, 17149-17151 (2011).
10. Weizmann, Y. et al. A Virus Spotlighted by an Autonomous DNA Machine. *Angew. Chem.*, Int. Ed. 45, 7384-7388 (2006).
11. Orbach, R., Mostinski, L., Wang, F. & Willner, I. Nucleic Acid Driven DNA Machineries Synthesizing $Mg^{2+}$-Dependent DNAzymes: An Interplay between DNA Sensing and Logic-Gate Operations. *Chem. Eur. J.* 18, 14689-14694 (2012).
12. Wang, F., Freage, L., Orbah, R. & Willner, I. Autonomous Replication of Nucleic Acids by Polymerization/Nicking Enzyme/DNAzyme Cascades for the Amplified Detection of DNA and the Aptamer-Cocaine Complex. *Anal. Chem.* 85, 8196-8203 (2013).
13. Tian, Y., He, Y. & Mao, C. Cascade Signal Amplification for DNA Detection. *ChemBioChem.* 7, 1862-1864 (2006).
14. Wen, Y. et al. DNAzyme-Based Rolling-Circle Amplification DNA Machine for Ultrasensitive Analysis of MicroRNA in *Drosophila* Larva. *Anal. Chem.* 84, 7664-7669 (2012).
15. Li, B., Jiang, Y. Chen, X. & Ellington, A. D. Probing Spatial Organization of DNA Strands using Enzyme-free Hairpin Assembly Circuits. *J. Am. Chem. Soc.* 134, 13918-13921 (2012).
16. Dirks, R. M, & Pierce, N. A. Triggered amplification by hybridization chain reaction. *Proc. Natl. Acad. Sci. U.S.A.* 101, 15275-15278 (2004).
17. Lin, Z. et al. An ultrasensitive colorimeter assay strategy for p53 mutation assisted by nicking endonuclease signal amplification. *Chem. Commun.* 47, 9069-9071 (2011).
18. Tian, T. et al. Sensitive and Convenient Detection of microRNAs Based on Cascade Amplification by Catalytic DNAzymes. *Chem. Eur. J.* 19, 92-95 (2013).
19. Bi, S., Zhang, J. & Zhang, S. Ultrasensitive and selective DNA detection based on nicking endonuclease assisted signal amplification and its application in cancer cell detectionw. *Chem. Commun.* 46, 5509-5511 (2010).
20. Zuo, X., Xia, F., Xiao, Y. & Plaxco, K. W. Sensitive and Selective Amplified Fluorescence DNA Detection Based on Exonuclease III-Aided Target Recycling. *J. Am. Chem. Soc.* 132, 1816-1818 (2010).
21. Gill, R., Zayats, M. & Willner, I. Semiconductor Quantum Dots for Bioanalysis. *Angew. Chem. Int. Ed.* 47, 7602-7625 (2008).
22. Frasco, M. F. & Chaniotakis, N. Semiconductor Quantum Dots in Chemical Sensors and Biosensors. *Sensors* 9, 7266-7286 (2009).

23. Peng, H. et al. DNA Hybridization Detection with Blue Luminescent Quantum Dots and Dye-Labeled Single-Stranded DNA. *J. Am. Chem. Soc.* 129, 3048-3049 (2007)
24. Niazov, A., Freeman, R., Girsh, J. & Willner, I. Following Glucose Oxidase Activity by Chemiluminescence and Chemiluminescence Resonance Energy Transfer (CRET) Processes Involving Enzyme-DNAzyme Conjugates. *Sensors* 11, 10388-10397 (2011).
25. Freeman, R., Liu, X. & Willner, I. Chemiluminescent and Chemiluminescence Resonance Energy Transfer (CRET) Detection of DNA, Metal Ions, and Aptamer-Substrate Complexes Using Hemin/G-Quadruplexes and CdSe/ZnS Quantum Dots. *J. Am. Chem. Soc.* 133, 11597-11604 (2011).
26. Sharon, E., Freeman, R., & Willner, I. CdSe/ZnS Quantum Dots-G-Quadruplex/Hemin Hybrids as Optical DNA Sensors and Aptasensors. *Anal. Chem.* 82, 7073-7077 (2010).
27. Freeman, R., Liu, X. & Willner, I. Amplified Multiplexed Analysis of DNA by the Exonuclease II-Catalyzed Regeneration of the Target DNA in the Presence of Functionalized Semiconductor Quantum Dots. *Nano Let.* 11, 4456-4461 (2011).
28. Cohen, S. et al. Protein Composition of Catalytically Active Human Telomerase from Immortal Cells. *Science.* 315, 1850-1853 (2007).
29. Bryan, T. M. & Cech, T. R. Telomerase and the maintenance of chromosome ends. Curr. *Opin. Cell Biol.* 11, 318-324 (1999).
30. Freeman, R. et al. DNAzyme-Like Activity of Hemin-Telomeric G-Quadruplexes for the Optical Analysis of Telomerase and its Inhibitors. *ChemBioChem.* 1, 2362-2367 (2010).
31. Freeman, R. et al. Optical Aptasensors for the Analysis of the Vascular Endothelial Growth Factor (VEGF). *Anal. Chem.* 84, 6192-6198 (2012)
32. Cohen, S. B. & Reddel, R. R. A sensitive direct human telomerase activity assay. *Nat. Methods.* 5, 355-360 (2008)
33. Kuprys, P. et al. Identification of Telomerase RNAs from Filamentous Fungi Reveals Conservation with Vertebrates and Yeasts. *PLoS One.* 8, e58661 (2013)
34. Yin, B. C. et al. One-Step, Multiplexed Fluorescence Detection of microRNAs Based on Duplex-Specific Nuclease Signal Amplification. *J Am Chem Soc.* 134, 5064-7 (2012)

What is claimed is:

1. A kit for detecting a target nucleic acid, comprising, in a reaction mixture:
    a polynucleotide probe;
    a nuclease;
    a telomerase; and
    a magnesium-containing buffer,
    wherein the polynucleotide probe comprises a polynucleotide connected to a nanoparticle and an acceptor at two ends of the polynucleotide, respectively, wherein the nanoparticle has an optical property and transfers energy to the acceptor to trigger-on a luminescence change, and wherein the acceptor is a luminescent dye or a quencher, and the polynucleotide comprises:
    a first sequence; and
    a second sequence complementary to the target nucleic acid,
    wherein the first sequence is a telomerase primer that is at least three continuous nucleotides complementary to CAAUCCCAAUC (SEQ ID NO. 1) and the second sequence is CCATCTTTACCAGACAGTGTTA (SEQ ID NO. 20).

2. The kit according to claim 1, wherein the nuclease is a duplex-specific nuclease.

3. The kit according to claim 1, wherein the reaction mixture further comprises an optically active molecule or hemin.

4. The kit according to claim 1 wherein the reaction mixture further comprises a reagent that contains luminal and $H_2O_2$ or contains ABTS and $H_2O_2$.

5. The kit according to claim 1, the telomerase primer is at least three continuous nucleotides selected from TTAGGG (SEQ ID NO. 6).

6. The kit according to claim 1, wherein the nanoparticle comprises one selected from the group consisting of core-type quantum dot, a core-shell quantum dot, an alloyed quantum dot and a combination thereof.

7. The kit according to claim 6, wherein the nanoparticle is a CdSe/ZnS quantum dot.

8. The kit according to claim 1, wherein the acceptor is BHQ2 or Cy5.

* * * * *